US006440894B1

(12) United States Patent
Martens et al.

(10) Patent No.: US 6,440,894 B1
(45) Date of Patent: Aug. 27, 2002

(54) METHODS OF REMOVING HALOGEN FROM NON-ZEOLITIC MOLECULAR SIEVE CATALYSTS

(75) Inventors: Luc R. Martens, Meise (BE); Stephen N. Vaughn, Kingwood, TX (US); Albert E. Schweizer, Baton Rouge, LA (US); John K. Pierce, Houston, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/891,674

(22) Filed: Jun. 25, 2001

(51) Int. Cl.[7] .............................. B01J 27/14; B01J 27/18; B01J 27/182
(52) U.S. Cl. ..................................... 502/214; 502/208
(58) Field of Search ................................. 502/208, 214

(56) References Cited

U.S. PATENT DOCUMENTS

| 4,681,864 A | | 7/1987 | Edward et al. ............... 502/63 |
|---|---|---|---|
| 4,859,314 A | * | 8/1989 | Pellet et al. ................. 208/114 |
| 4,914,067 A | * | 4/1990 | Pellet et al. ................. 208/114 |
| 4,973,792 A | | 11/1990 | Lewis et al. ................. 585/638 |
| 5,095,163 A | | 3/1992 | Barger ........................ 585/640 |
| 5,248,647 A | | 9/1993 | Barger ........................ 502/214 |
| 5,776,849 A | | 7/1998 | Fung et al. .................... 502/37 |
| 5,980,731 A | | 11/1999 | Kao et al. .................... 208/137 |
| 6,153,522 A | | 11/2000 | Wachter et al. ............. 502/280 |

FOREIGN PATENT DOCUMENTS

WO    WO 99/21651    *   5/1999

* cited by examiner

*Primary Examiner*—Elizabeth D. Wood
(74) *Attorney, Agent, or Firm*—James Sher (57) ABSTRACT

Methods of calcining non-zeolitic molecular sieve catalyst to remove most, if not nearly all, of halogen contained in the catalyst. One method includes heating the catalyst in a low moisture environment, followed by contacting the heated catalyst with air and/or steam. Another method includes steam-treating the catalyst at a temperature from 400° C. to 1000° C. The calcination methods provides a catalyst that contains from about 10 ppmw to about 600 ppmw chlorine, preferably 10 ppmw to about 200 ppmw chlorine, more preferably 10 ppmw to about 80 ppmw chlorine.

57 Claims, 1 Drawing Sheet

METHODS OF REMOVING HALOGEN FROM NON-ZEOLITIC MOLECULAR SIEVE CATALYSTS

FIELD OF THE INVENTION

The present invention relates to methods of removing halogen from non-zeolitic, molecular sieve catalysts, the catalysts produced from such methods, and the use of such catalysts in an oxygenate to olefin processes.

BACKGROUND OF THE INVENTION

Molecular sieve catalysts used in a fluidized-bed reactor or a riser reactor will typically have an average particle diameter from 40 μm to 300 μm. Catalyst particle size within this range is needed for proper fluidization as well as to efficiently separate the catalyst from the gaseous products in a cyclone separator. To maintain the desired catalyst diameter the molecular sieve is formulated with other materials. Dilution of the molecular sieve with these materials is also used to control the rate of reaction, control the temperature of the reactor and regenerator, and to stabilize and protect the molecular sieve.

Formulated molecular sieve catalysts present a problem not found in other types of industrial catalysts, that is, how to maintain the physical integrity of the molecular sieve catalyst during the fluidized cyclic process of reaction, separation, and regeneration. The cycles of reaction, separation, and regeneration are carried out at high temperatures and high flow rates. Collisions and abrasions between catalyst particles, between the catalyst particles and reactor walls and between the catalyst particles and other parts of the unit tend to cause physical breakdown of the original catalyst into smaller catalyst particles known as fines. This physical breakdown is referred to as catalyst attrition. The fines usually have particle diameters smaller than 20 microns—much smaller than the original catalyst particles. Catalysts with higher attrition resistance are desirable because, among other reasons, fewer fines are generated for disposal, less environmental impact is caused by unrecoverable airborne particulates, optimal fluidized conditions are maintained, operating costs are lower, and less replacement catalyst is required.

Molecular sieve catalysts are formed by various methods, for example, by spray drying or extruding a slurry containing the molecular sieve and the other catalyst components. The catalysts are formed by mixing the zeolitic molecular sieve with one or more binding agents such as one or more types of alumina and/or silica. Matrix materials, typically clays, are also added and serve as diluents to control the rate of the catalytic reaction, and to facilitate heat transfer during many stages of the process. In U.S. Pat. No. 5,346,875 to Wachter et al. zeolite-Y (21.8 wt %) is mixed with Kaolin clay (14.5 wt %), silica sol (48.3 wt %), and Reheis chlorhydrol (15.4 wt %) to form a slurry which is then spray dried and calcined. A conventional calcination procedure was used; heating at 550° C. in air for 2 hours.

Non-zeolitic, molecular sieve catalysts are known to convert oxygenates, particularly methanol, to light olefins. The oxygenate to olefin process includes separate processing zones for conducting the catalytic reaction, product-catalyst separation, and catalyst regeneration. The produced olefin and other hydrocarbon products are separated from the catalyst particles in a separator, suitably a cyclone separator. A portion of the catalyst is recovered from the separator and passed to a regenerator. In the regenerator the non-zeolitic molecular sieve catalyst contacts a combusting gas, e.g. air, at a temperature sufficient to burn off carbon deposits, commonly referred to a coke, that accumulate on the surface and in the pores of the catalyst. The regenerated catalyst is then returned to the oxygenate conversion reactor.

In this process, the non-zeolitic molecular sieve catalyst is subjected to great mechanical stresses. As the catalyst is transferred from the reaction zone to cyclone separators, to regenerators, and finally back to the reaction zone the catalyst will tend to disintegrate into catalyst fines. These catalyst fines must be removed from the reactor process and discarded. No matter how resistant the catalyst is to attrition, eventually the oxygenate to olefin process will break down the non-zeolitic molecular sieve catalyst because the catalyst moves through the system at such high speeds. The resistance of the catalyst to attrition is an important property of the catalyst.

In PCT Publication No. WO 99/21651 to Wachter et al. and U.S. Pat. No. 4,973,792 to Lewis et al., silicoaluminophosphate (SAPO) molecular sieve catalysts were produced by preparing a slurry containing SAPO-34, Kaolin clay, and Reheis chlorhydrol. The slurry was then directed to a spray dryer to form catalyst particles with the desired size. The spray dried catalysts were calcined, however the conditions of the calcination were stated to be not critical.

In U.S. Pat. No. 5,248,647 and 5,095,163 to Barger et al. SAPO molecular sieve is mixed with an aqueous silica sol and spray dried. The spray dried catalyst is mixed with an aqueous solution of ammonium sulfate at 60° C. three times, then washed with water and dried at 100° C. The dried, ion-exchanged catalyst is then calcined in air at 550° C. for over 3.3 hours and then the temperature is lowered to ambient room temperature over a period of 2 hours. A portion of this catalyst is then contacted with steam at 725° C. or 750° C. for 10 hours. Steam treatment following calcination is shown to increase catalyst life, increase selectivity to ethylene and propylene, and decrease selectivity to propane.

If SAPO molecular sieve catalysts are ever going to be used commercially to convert oxygenates to olefins, catalysts with greater attrition properties are needed. For this reason, the Applicants' sought to develop SAPO catalysts with a relatively high resistance to attrition.

SUMMARY OF THE INVENTION

The present invention is directed to methods of removing a portion of the halogen present in non-zeolitic molecular sieve catalysts. One embodiment of removing halogen includes heating the catalyst in a low moisture environment at a temperature from about 400° C. to about 1000°, and contacting the heated catalyst with steam at a temperature from about 400° C. to about 1000° C. to produce a steam-treated catalyst. Preferably, the low moisture environment contains less than 5% by volume, more preferably less than 1% by volume, water. The steam treatment can take place in an oxygen environment. Also, it is preferred that the steam treatment take place in an environment containing at least 10% by volume water. In the preferred embodiment, the steam treatment can remove from about 50% to about 99% by weight, more preferably from about 90% to about 99% by weight, of halogen from the heated catalyst. The method can be used to remove halogen from silicoaluminophosphate and/or aluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, or mixtures thereof.

In another embodiment, a portion of the halogen can be removed from a non zeolitic molecular sieve catalyst by heating the catalyst in an oxygen environment at a temperature from about 400° C. to about 1000° C. to produce a heated catalyst, and contacting the heated catalyst with steam at a temperature from about 400° C. to about 1000° C. Preferably, the oxygen environment contains greater than about 10% by volume oxygen. It is also preferred, that the steam treatment take place in an environment containing at least about 10% by volume water. In many cases, the halogen to be removed will be chlorine, and preferably from about 70% to about 99% by weight, more preferably from about 90% to about 99% by weight, of the chlorine will be removed from the heated catalyst.

In another embodiment, a portion of the halogen can be removed from a non zeolitic molecular sieve catalyst by calcining the catalyst in an environment containing steam at a temperature from about 400° C. to about 1000° C., preferably from about 500° C. to about 800° C., and more preferably from about 550° C. to about 700° C., to remove from about 70% to about 99.99% by weight of the halogen from the catalyst. If the halogen to be removed from the catalyst is chlorine, the likely source of the chlorine is aluminum chlorhydrol that is used to produce the catalyst. The environment can contain from 5% to about 10% by volume water, or at least 10% by volume, water. The environment can further contain air, nitrogen, helium, flue gas, or any combination thereof.

In one embodiment, the catalyst is heated in a low-moisture environment at a temperature of from about 400° C. to about 1000° C. to remove at least about 50% by weight of the halogen in the catalyst prior to steam treatment. Preferably, the low moisture environment contains less than about 5% by volume, more preferably less then about 1% by volume, water. Also, the steam-treated catalyst can optionally be heated in an oxygen environment that contains greater than about 5% by volume oxygen.

In another embodiment, a portion of the halogen can be removed from a silicoaluminophosphate molecular sieve catalyst by heating the catalyst in a low moisture environment at a temperature from 400° C. to about 1000° C. to remove at least about 50% by weight of the chlorine from the catalyst, followed by contacting the heated catalyst in a second calcination environment containing about 5% to about 10% by volume water at a temperature from 400° C. to about 1000° C. Preferably, the low moisture environment contains less than about 1% by volume water.

The invention is also directed to a catalyst containing a non zeolitic molecular sieve, inorganic oxide matrix, and matrix material, wherein the catalyst contains from about 10 ppmw to about 600 ppmw by weight halogen. Generally, the halogen is chlorine, and the catalyst will contain from about 10 ppmw to about 200 ppmw, preferably from about 10 ppmw to about 80 ppmw, chlorine. It is also preferred that the catalyst have a GAL Index of less than about 5, more preferably less than about 3, most preferably less than about 2. The non-zeolitic molecular sieve in the catalyst is preferably selected from SAPO-5, SAPOL8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, or mixtures thereof. Preferably, the catalyst contains about 20% to about 45% by weight, more preferably from about 25% to about 42% by weight, non-zeolitic molecular sieve, about 5% to about 20% by weight, more preferably about 8% to about 15% by weight, of inorganic oxide matrix, and about 20% to about 70% by weight, more preferably from about 40% to about 60% by weight, matrix material. In the preferred embodiment, the inorganic oxide matrix contains an aluminum oxide matrix that is formed from the heat treatment of aluminum chlorhydrol.

BRIEF DESCRIPTION OF THE DRAWINGS

The present invention will be better understood by reference to the Detailed Description of the Invention when taken together with the attached drawing, wherein.

DETAILED DESCRIPTION OF THE INVENTION

To produce non-zeolitic molecular sieve catalyst with a relatively high resistance to attrition, an inorganic oxide sol that contains halogen can be used. A preferred route to produce non-zeolitic molecular sieve catalyst is to use an alumina sol that contains chlorine, more preferably aluminum chlorhydrol, as a binder. The inorganic oxide sol functions as a "glue" which binds the catalyst components together. However, using an inorganic oxide sol that contains halogen presents a problem not associated with the use of halogen-free binders. A portion of the halogen from the inorganic oxide sol remains in the formed catalyst. It is desirable to remove most, if not nearly all, of the halogen from the catalyst before the catalyst is used in the oxygenate to olefin process. If most of the halogen is not removed from the catalyst, halogen-containing acids will form in the oxygenate to olefin reactor. Over time, the released acid will corrode the oxygenate to olefin reactor and other process units. While the invention will be further illustrated for the case where the halogen is chlorine, it should be understood that the invention applies to other halogens as well, such as fluorine, bromine and iodine. In the case of a catalyst containing chlorine, hydrochloric acid will form in the oxygenate to olefin reactor. HCl may be in the gas or condensed form, usually in a hydrated form, hereinafter referred to as $HCl_{(aq)}$. All forms of acids are potentially corrosive, the hydrated form being the most corrosive.

The invention addresses the problem associated with the use of inorganic oxide sols that contains halogen by removing much of the halogen from the catalyst during calcination of the catalyst. The invention addresses these problems by providing methods of heat treating or calcining a formed non-zeolitic molecular sieve catalyst prepared with an inorganic oxide sol that contains halogen. The methods of the invention minimize the production of halogen-containing acids, or at least confines much of the produced halogen-containing acids to a single heating or calcination unit that can be designed to accommodate the corrosive effects of halogen-containing acids. The methods of the invention also reduce the amount of halogen remaining in the catalyst over that of conventional procedures.

The catalyst is made by preparing a slurry containing non-zeolitic molecular sieve, an inorganic oxide binder, and a matrix material. The slurry is then dried and shaped in a forming unit. Preferably, the slurry is spray dried, and a dry powder catalyst with an average catalyst particle size is obtained. The formed catalyst is then heat treated, i.e., calcined.

Calcination is used to remove the template molecule from the cage structure of the framework. During calcination all or part of the template molecule exits the cage structure. Calcination is also used to harden the formed catalyst particle. The relatively high temperatures used during calcination transform the inorganic oxide sol to an inorganic oxide matrix. It is this inorganic oxide matrix that increases the attrition resistance of the catalyst particle.

If a conventional calcination procedure is used on a catalyst containing chlorine, that is, heating in air at temperatures greater than 400° C., large amounts of HCl are produced over time in the calcination unit. The formation of $HCl_{(aq)}$ is the result of small amounts of water or water vapor contained in the air and the water generated from the oxidative combustion of the organic template during calcination. The released HCl, if not accounted for, will eventually corrode the heating or calcination unit. Therefore, it is desirable to control the removal of chlorine from the catalyst in a manner that will either minimize the amount of HCl produced during the calcination process or limit the evolution of HCl to a single calcination unit.

A conventional calcination procedure also does not remove enough of the halogen from the catalyst. In the case of chlorine, the remaining chlorine in the catalyst is then released into the oxygenate to olefin reactor and other oxygenate to olefin process units as $HCl_{(aq)}$ due to the hydrothermal conditions of the oxygenate to olefin process. If not accounted for, the release of this $HCl_{(aq)}$ will corrode the oxygenate to olefin process units. The presence of $HCl_{(aq)}$ in the olefin monomer feed used for polymerization might also damage or poison expensive polymerization catalysts. Therefore, it is desirable to remove as much chlorine from the catalyst during the calcination process so as to minimize the amount of $HCl_{(aq)}$ released into the oxygenate to olefin process units.

As a result of using the calcination methods of the invention, a non-zeolitic molecular sieve catalyst with low amounts of halogen is obtained. A preferred catalyst of the invention contains a SAPO molecular sieve, an aluminum oxide matrix, and clay, most preferably Kaolin. The catalyst will also contain some halogen resulting from the use of a binder that contains halogen. Although the invention is directed to removing as much halogen from the catalyst as efficiently possible, some of the halogen is not removed during the calcination process. Following the calcination procedures of the invention, the catalyst will contain from about 10 ppmw to 600 ppmw halogen, preferably from about 10 ppmw to 200 ppmw halogen, more preferably from about 10 ppmw to 60 ppmw halogen. The catalyst will also have a Gross Attrition Loss (GAL) Index of less than 5, preferably a GAL Index less than 3, more preferably a GAL Index less than 2. The smaller the GAL Index, the more resistant to attrition is the catalyst.

1. Non Zeolitic Molecular Sieve

The catalyst used according to the present invention contains a non zeolitic molecular sieve. Examples of suitable non-zeolitic molecular sieves are silicoaluminophosphates (SAPOs) and aluminophosphates (ALPOs). In general, SAPO molecular sieves comprise a molecular framework of corner-sharing $[SiO_4]$, $[AlO_4]$, and $[PO_4]$ tetrahedral units. The $[PO_4]$ tetrahedral units are provided by a variety of compositions. Examples of these phosphorus-containing compositions include phosphoric acid, organic phosphates such as triethyl phosphate, and aluminophosphates. The $[AlO_4]$ tetrahedral units are provided by a variety of compositions. Examples of these aluminum-containing compositions include aluminum alkoxides such as aluminum isopropoxide, aluminum phosphates, aluminum hydroxide, sodium aluminate, and pseudoboehmite. The $[SiO_4]$ tetrahedral units are provided by a variety of compositions. Examples of these silicon-containing compositions include silica sols and silicium alkoxides such as tetra ethyl orthosilicate. The phosphorus-, aluminum-, and silicon-containing compositions are mixed with water and a template molecule and heated under appropriate conditions to form the molecular sieve.

SAPO molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 Angstroms to about 10 Angstroms, and are capable of molecular size selective separations of molecular species. More than two dozen structure types have been reported, including zeolite topological analogues.

For a catalyst used in the conversion of oxygenate to light olefin the non-zeolitic molecular sieve will have a relatively low $Si/Al_2$ ratio. In general, for SAPOs, a $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Substituted SAPOs and ALPOs can also be used in this invention. These compounds are generally known as MeAPSOs, MeAPOs, metal-containing silicoaluminophosphates or metal-containing aluminophosphates. The metal can be alkali metal ions (Group IA), alkaline earth metal ions (Group IIA), rare earth ions (Group IIIB, including the lanthanide elements, and the additional transition cations of Groups IB, IIB, IVB, VB, VIB, VIIB, and VIIIB. Preferably, the Me represents atoms such as Zn, Ni, and Cu. These atoms can be inserted into the tetrahedral framework through a $[MeO_2]$ tetrahedral unit. Incorporation of the metal component is typically accomplished by adding the metal component during synthesis of the molecular sieve. However, post-synthesis metal incorporation can also be used.

SAPO and ALPO molecular sieves that can be used include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms thereof, and mixtures thereof. Preferred are SAPO-18, SAPO-34, SAPO-35, SAPO-44, SAPO-56, ALPO-18 and ALPO-34, particularly SAPO-18, SAPO-34, ALPO-34 and ALPO-18, including the metal containing forms thereof, and mixtures thereof. As used herein, the term mixture is synonymous with combination and is considered a composition of matter having two or more components in varying proportions, regardless of their physical state.

SAPO and ALPO molecular sieves are synthesized by hydrothermal crystallization methods generally known in the art. See, for example, U.S. Pat. Nos. 4,440,871; 4,861,743; 5,096,684; and 5,126,308, the disclosures of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed.

Formation of the crystalline product can take anywhere from around 2 hours to as much as 2 weeks. In some cases, stirring or seeding with crystalline material will facilitate the formation of the product. Typically, the molecular sieve product is formed in solution. It can be recovered by standard means, such as by centrifugation or filtration. The product can also be washed, recovered by the standard means, and dried. In one method, the molecular sieve is washed and collected by a filtration process that maintains the molecular sieve in slurry form. This process includes adding wash fluid as the molecular sieve is concentrated from the synthesis solution.

Additional molecular sieve materials can be included as a part of the non zeolitic molecular sieve catalyst composition or they can be used as separate molecular sieve catalysts in admixture with the non zeolitic molecular sieve catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types,* W. M. Meier and D. H. Olsen, Butterworth Heineman, 3rd ed., 1997, the detailed description of which is explicitly incorporated herein by reference. Preferred molecular sieves which can be combined with a silicoaluminophosphate and/or an aluminophosphate catalyst include ZSM-5, ZSM-34, erionite, and chabazite.

2. Binders

Once the desired type or types of non-zeolitic molecular sieve is selected based upon the desired activity and selectivity of the catalyst, other materials are blended with the non-zeolitic molecular sieve. One of these materials includes one or more binders, such as a type of hydrated alumina, and/or an inorganic oxide sol such as aluminum chlorhydrol. The inorganic oxide sol is essentially a "glue" which binds the catalyst components together upon thermal treatment. After the formed catalyst particle is formed and heated, the inorganic oxide sol is converted to an inorganic oxide matrix component. For example, an alumina sol will convert to an aluminum oxide matrix following a heat treatment of the formed catalyst. Aluminum chlorhydrol is a hydroxylated aluminum based sol containing chloride as the counter ion. Aluminum chlorhydrol has the general formula of $Al_mO_n(OH)_oCl_p \cdot xH_2O$ wherein m is 1 to 20, n is 1 to 8, o is 5 to 40, p is 2 to 15, and x is 0 to 30. Although the equilibria of alumina species in the sol is complex, the predominant species is believed to be $[Al_{13}O_4(OH)_{24}Cl_7(H_2O)_{12}]$. In addition, other alumina materials may be added with the aluminum chlorhydrol. Materials that can be used include, but are not necessarily limited to aluminum oxyhydroxide, γ-alumina, boehmite, diaspore, and transitional aluminas such as α-alumina, β-alumina, γ-alumina, δ-alumina, ε-alumina, κ-alumina, and ρ-alumina. Aluminum trihydroxide, such as gibbsite, bayerite, nordstrandite, doyelite, and mixtures thereof, also can be used. A sufficient amount of the binder is added to the slurry mixture so that the amount of the resultant inorganic oxide matrix in the catalyst, not including the inorganic oxide framework of the non-zeolitic molecular sieve, is from about 2% to about 30% by weight, preferably from about 5% to about 20% by weight, and more preferably from about 7% to about 12% by weight.

3. Matrix Materials

The non zeolitic molecular sieve catalysts will also contain clay, preferably Kaolin. Matrix materials may also include compositions such as various forms of rare earth metals, metal oxides, titania, zirconia, magnesia, thoria, beryllia, quartz, silica or silica or silica sol, and mixtures thereof. The added matrix materials components are effective in reducing, inter alia, overall catalyst cost, acting as a thermal sink to assist in heat shielding the catalyst during regeneration, densifying the catalyst and increasing catalyst strength. The use of matrix materials such as naturally occurring clays, e.g., bentonite and kaolin, improves the crush strength of the catalyst under commercial operating conditions. Thus, the addition of clays improve upon the attrition resistance of the catalyst. The inactive materials also serve as diluents to control the rate of conversion in a given process so that more expensive means for controlling the rate of reaction is eliminated or minimized. Naturally occurring clays which can be used in the present invention include the montmorillonite and kaolin families which include the sabbentonites, and the kaolins, commonly known as Dixie, McNamee, Georgia and Florida clays, or other in which the main mineral constituent is haloysite, kaolinite, dickite, nacrite, or anauxite.

As with most catalysts clay is used in the invention as an inert densifier, and for the most part the clay has no effect on catalytic activity or selectivity. Kaolin's ability to form pumpable, high solid content slurries, low fresh surface area, and ease of packing because of its platelet structure makes it particularly suitable for catalyst processing. The preferred average particle size of the kaolin is 0.1 μm to 0.6 μm with a D90 particle size of about 1 μm. Because of environmental concerns, the crystalline silica content of the clay has also become an important parameter.

4. Mixing and Spray Drying

Rigorous mixing of the catalyst components is necessary to produce a hard, dense, homogeneous catalyst particle. The primary consequence of poor mixing are poor attrition and poor catalyst density. Stratification of the components caused by incomplete mixing can also effect the activity and selectivity of the catalyst. Generally, the mixers are of a high shear type because of the thixotropic nature of the slurries. The resultant slurry may be colloid-milled for a period sufficient to obtain a desired sub-particle texture, sub-particle size, and/or sub-particle size distribution.

The catalyst particle contains a plurality of catalyst sub-particles. The average diameter of the catalyst particle is from 40 μm to 300 μm, preferably from 50 μm to 200 μm. The catalyst sub-particles contain non-zeolite molecular sieve, typically SAPO molecular sieve, an aluminum oxide matrix, and a matrix material, typically clay. Preparation of the catalyst begins with mixing one or more non-zeolite molecular sieve, one or more inorganic oxide sols, one or more matrix materials, and a fluid, typically water, to form a slurry. Other fluids, e.g., alcohol, can be used along with the water.

The preferred slurry is prepared by mixing the non-zeolitic molecular sieve with aluminum chlorhydrol and Kaolin clay, together or in sequence, in dry form or as slurries. If the solids are added together as dry solids, a limited and controlled amount of water is added. The slurry may also contain other materials including other forms of molecular sieve, other binders, and other matrix materials. The mesoporosity of the catalyst and the mechanical strength of the catalyst is dependent on the amount of water contained in the slurry. In general, it has been found that the weight percent of solids in the slurry can range from 20% to 70% by weight, preferably from 40% to 60% by weight. When the weight percent of solids in the slurry is greater than 70% by weight, the viscosity of the slurry is too high to spray dry, and when the weight percent of solids in the slurry is less than 20% by weight the attrition resistance of the catalyst is poor. It is also desirable that the density of the slurry be greater than 1.1 g/cc, and preferably greater than 1.18 g/cc to form the catalysts of this invention.

The solid content of the slurry will contain about 10% to about 50%, preferably about 20% to about 45% by weight, non-zeolitic molecular sieve, 5 about 5% to about 20%, preferably from about 8% to about 15% by weight, binder, and about 30% to about 80%, preferably about 40% to about 60% by weight, matrix material. The slurry is mixed or milled to achieve a sufficiently uniform slurry of catalyst sub-particles. The slurry is then fed to a forming unit to produce catalyst particles. The forming unit is maintained at a temperature sufficient to remove most of the water from the formed catalyst particles. Preferably, the forming unit is a spray dryer. The formed catalyst particles typically take the form of microspheres. Typically, the slurry is fed to a spray drier at an average inlet temperature ranging from 200° C. to 450° C., and an outlet temperature ranging from 100° C. to about 225° C.

During spray drying, the slurry is passed through a nozzle which distributes the slurry into small droplets, resembling an aerosol. A single nozzle unit or multiple nozzle unit may be used to disperse an inlet stream of slurry (single-fluid nozzle) into the atomization chamber. Alternatively, a multiple nozzles may be used to co-feed the slurry into the atomization chamber. Alternatively, the slurry is directed to the perimeter of a spinning wheel which also distributes the slurry into small droplets. The size of the distributed slurry droplets is controlled by many factors including flow rate, pressure, and temperature of the slurry, the shape and dimension of the nozzle(s), or the spinning rate of the wheel. The droplets are then dried in a co-current or counter-current flow of air passing through the spray drier. Dry catalyst particles in the form of a powder are recovered from each droplet.

Catalyst particle size to some extent is controlled by the solids content of the slurry and its viscosity. All else being equal, the catalyst particle size is directly proportional to the solids content of the slurry. However, control of the catalyst particle size and spherical characteristics also depend on the size and shape of the drying chamber as well as the atomization procedure used. A Boltzmann distribution of catalyst particle size is invariably obtained around a mean, which is usually set at approximately 70 μm average catalyst particle size. The average catalyst particle size is controlled by a variation in the slurry feed properties to the dryer and by the conditions of atomization. It is preferred that the formulated catalyst composition have a catalyst size from 40 μm to 300 μm, more preferably 50 μm to 200 μm, most preferably 50 μm to 150 μm.

5. Calcination

To harden and/or activate the formed catalysts a heat treatment, i.e., calcination, at an elevated temperature is usually necessary. Ordinarily, catalysts with alumina or silica binders are heated in a calcination environment at a temperature between 500° C. and 800° C. The conventional calcination environment is air, which may include small amounts of water vapor.

Figure 1:
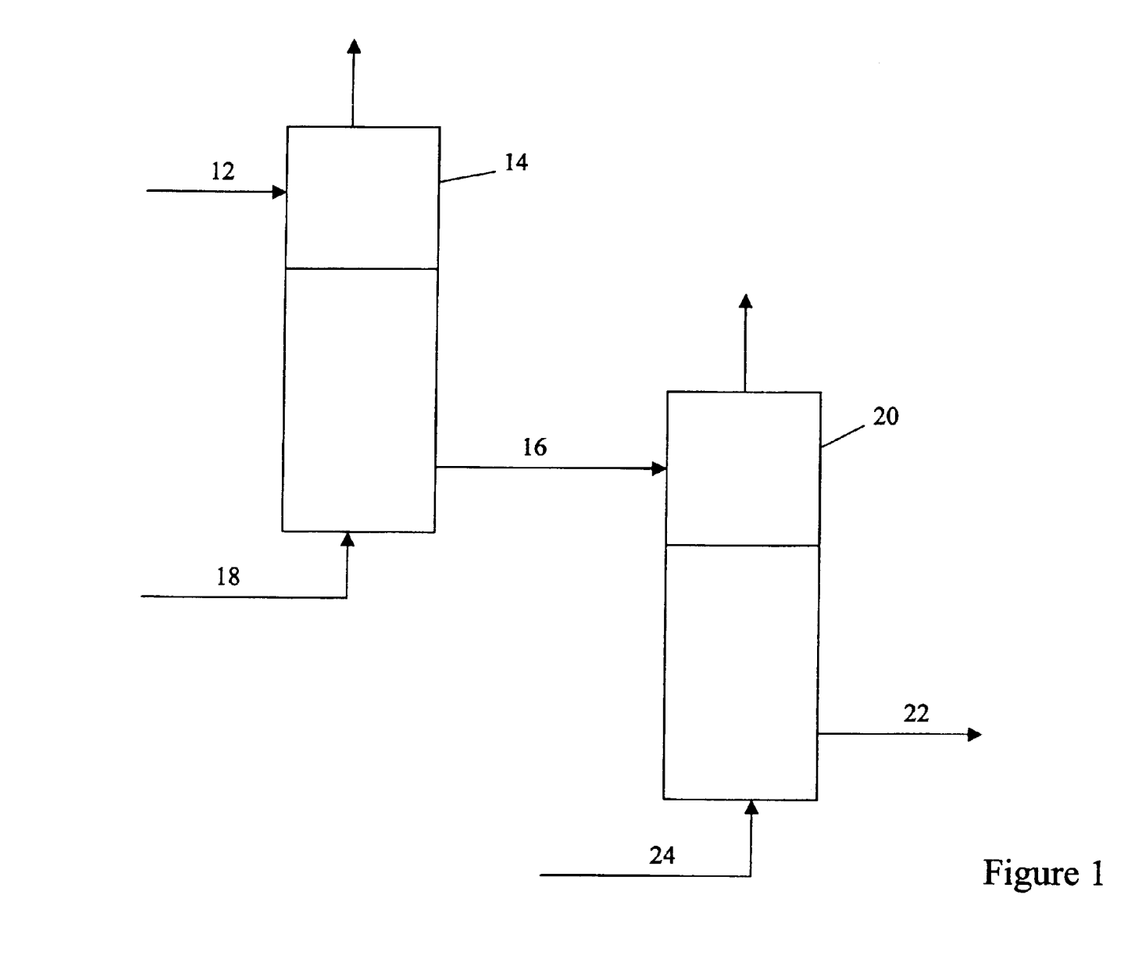
FIG. 1 is a schematic representation of one embodiment for removing chlorine from a formed catalyst.

The invention provides methods of heat treating a formed non-zeolitic molecular sieve catalyst prepared with an inorganic oxide sol that contains halogen. The methods of the invention minimize the production of halogen-containing acids or at least confines much of the produced halogen-containing acids to a single heating unit. The schematic diagram in FIG. 1 depicts one embodiment of the invention, in which a chlorine-containing SAPO catalyst 12 is used by way of example. Catalyst 12 is supplied from a forming unit, preferably a spray dryer, and is directed to a heat treatment unit 14. The catalyst is heated at a temperature from about 400° C. to about 1000° C., preferably from about 500° C. to about 800° C., most preferably from about 550° C. to about 700° C. in a low moisture calcination environment containing less than 5% by volume water, preferably less than 1% by volume water. The low moisture calcination environment can be provided by using a dry gas 18, e.g., air that has been adequately dried, nitrogen, helium, flue gas, or any combination thereof. In the preferred embodiment, the catalyst is heated in nitrogen off gas at a temperature from about 600° C. to about 700° C. Nitrogen off gas is the gas produced from the boil-off gas of a liquid nitrogen source. Heating is carried out for a period of time sufficient to remove chlorides, typically for a period of from 0.5 to 10 hours, preferably of from 1 to 5 hours, most preferably from 2 to 4 hours.

As the catalyst is heated in the low moisture calcination environment most of the chlorine is removed as chlorine gas or as a non-hydrated form of hydrochloric acid ($HCl_{(g)}$). $HCl_{(g)}$ is not as corrosive as $HCl_{(aq)}$. Approximately 60% to 98% by weight, preferably 85% to 98% by weight, of the chlorine in the formed catalyst 12 is removed during the heat treatment in the low moisture calcination environment. Following this heat treatment the catalyst 16 contains less than about 6000 ppmw chlorine, preferably less than about 3000 ppmw chlorine.

Following the low moisture heat treatment, the catalyst 16 is directed to heating unit 20. The catalyst in heating unit 20 is heated in a second calcination environment 24. This second calcination environment 24 contains from about 5% to about 10% by volume water. The remaining volume of gas in the calcination environment 24 may include air, nitrogen, helium, flue gas, or any combination thereof. The second heat treatment of the catalyst 16 will take place at a temperature from about 400° C. to about 1000° C., preferably from about 500° C. to about 800° C., more preferably from about 600° C. to about 700° C. The period during which the catalysts is heated in unit 20 ranges from 0.1 to 5 hours, preferably from 0.25 to 4 hours. This second heat treatment results in a loss of about 2% to about 95% of the chlorine remaining in catalyst 16. Catalyst 22 will contain less than about 600 ppmw chlorine, preferably less than about 200 ppmw chlorine, more preferably less than about 80 ppmw chlorine.

In another embodiment, the second calcination environment contains at least 10% by volume water. The remaining volume of gas in the second calcination environment may include air, nitrogen, helium, flue gas, or any combination thereof. Preferably, the second calcination environment contains air. A catalyst that is contacted with a calcination environment containing at least 10% by volume water is said to be steam-treated. Steam treatment results in a loss of about 50% to 99%, preferably in a loss of about 90% to about 99% of the chlorine remaining in the catalyst following the low moisture heat treatment. The steam-treated catalyst will contain about 10 ppmw to about 400 ppmw chlorine, preferably about 10 ppmw to about 200 ppmw chlorine, more preferably about 10 ppmw to about 80 ppmw chlorine.

Steam treatment of the catalyst will take place at a temperature from about 400° C. to about 1000° C., preferably from about 500° C. to about 800° C., more preferably from about 600° C. to about 700° C. The period during which the catalysts is heated in unit 20 ranges from 0.1 to 5 hours, preferably from 0.25 to 4 hours. Although temperatures of about 400° C. are sufficient to adequately remove most of the chlorine from the catalyst, the rate at which the additional chlorine is removed will be lower than if a higher temperature, e.g., 600° C., is used during steam treatment. On the other hand, if the temperature of the steam treatment is too high, e.g., greater than 1000° C., degradation of the catalyst may occur. The temperature at which degradation of the catalyst will occur will vary for different catalyst formulations and various non-zeolitic molecular sieve.

The low moisture heat treatment followed by steam treatment can remove about 70% to about 99.99% by weight, preferably about 95% to about 99.99% by weight, more preferably about 98% to about 99.99% by weight, of the chlorine in the formed catalyst. The steam treatment will produce $HCl_{(aq)}$, but the amount of $HCl_{(aq)}$ produced is significantly reduced because most of the chlorine is removed during the initial heat treatment in the low moisture calcination environment. As a result, the production of the $HCl_{(aq)}$ is minimized. Also, if separate heating units are used the production of $HCl_{(aq)}$ will be confined to the steam treatment unit, which can be designed to accommodate the $HCl_{(aq)}$ produced.

If air is not used in the steam treatment, the catalyst may be calcined in a calcination environment containing at least 3% by volume, preferably at least 10% by volume, oxygen to remove template material that may have remained in the pores of the sieve. A catalyst that has been calcined in an environment that contains at least 3% by volume oxygen is said to be oxygen treated. The oxygen environment may be provided by air or a mixture of air and nitrogen. The calcination temperature of this oxygen environment may be the same or different than the temperature of the steam treatment.

It is to be understood that although FIG. 1 depicts more than one heating unit for each type of heat treatment, a single heating unit may be used. In this case, the heating environment is changed by alternating the type of gas flow, e.g., from nitrogen off gas to steam, or from air to steam. Alternatively, different heating zones in a singular heating unit may be used according to the invention. Each heating zone will contain a different calcination environment with a transition zone disposed between the heating zones. The temperature and gas flow for each heating zone or heating unit can be programmed to minimize the time required to remove the desired amount of chlorine, while minimizing the amount of $HCl_{(aq)}$ produced. The heat and steam treatments may be done in any of a number of heating units well known to those skilled in the art including moving bed reactors, rotary kilns, rotary calciners, fluidized beds and packed-bed batch reactors.

In another embodiment the steam treatment is used to remove most of the halogen from the formed catalyst. Prior heating in a low moisture environment is not necessary. The formed catalyst is steam-treated at a temperature from about 400° C. to about 1000° C., preferably from about 500° C. to about 800° C., more preferably from about 600° C. to about 700° C. The period during which the catalysts is heated in unit 20 ranges from 0.1 to 5 hours, preferably from 0.25 to 4 hours. The steam treatment may remove from about 70% to about 99.99% by weight, preferably from about 95% to about 99.99% by weight, more preferably from about 98% to about 99.99% by weight, of the chlorine in the formed catalyst.

Following the steam treatment, the catalyst may be oxygen treated to remove template material that may have remained in the pores of the sieve. The calcination temperature of this oxygen environment may be the same or different than the temperature of the steam treatment.

In another embodiment, steam treatment of the catalyst may take place after an oxygen heat treatment. The catalyst is heated in an oxygen environment at a temperature from 400° C. to 1000° C., preferably from about 500° C. to about 800° C., more preferably from about 600° C. to about 700° C. The period during which the catalysts is heated in unit 20 ranges from 0.1 to 5 hours, preferably from 0.25 to 4 hours. Approximately 50% to 95% by weight, preferably 75% to 95% by weight, of the chlorine in the formed catalyst is removed during the oxygen heat treatment. The oxygen treated catalyst is then contacted with steam to remove additional amounts of chlorine from the catalyst. This steam contacted catalyst will contain about 10 ppmw to about 600 ppmw chlorine, preferably 10 ppmw to about 200 ppmw chlorine, more preferably 10 ppmw to about 80 ppmw chlorine.

The oxygen heat treatment and the steam treatment of the catalyst may take place in separate heating units or in the same heating unit though in different regions of that unit. For example, the oxygen environment may be introduced near the entrance to the heating unit and steam added near the middle of the heating unit. In this way partial calcination of the catalyst occurs prior to the catalyst contacting the steam.

The catalysts of the invention are well suited for catalytically converting oxygenates to olefins. Any standard reactor system can be used, including fixed bed, fluid bed or moving bed systems. These and other types of conventional reactors are described in *Fluidization Engineering*, D. Kunii and O. Levenspiel, Robert E. Krieger Publishing Co. NY, 1977. Preferred reactors are riser reactors. Conventional riser reactor design is further described in "Riser Reactor," *Fluidization and Fluid-Particle Systems*, pages 48–59, F. A. Zenz and D. F. Othmo, Reinhold Publishing Corp., NY 1960, the description of which is incorporated herein by reference. Preferred reactors are co-current riser reactors and short contact time, countercurrent free-fall reactors.

Desirably, the reactor is one in which an oxygenate feedstock can be contacted with a molecular sieve catalyst according to the invention at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to 1000 $hr^{-1}$, and most preferably in the range of from about 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

The process can generally be carried out at a wide range of temperatures. An effective operating temperature range can be from about 200° C. to 700° C., preferably from about 300° C. to 600° C., more preferably from about 350° C. to 550° C. At the lower end of the temperature range, the formation of the desired olefin products may become markedly slow. At the upper end of the temperature range, the process may not form an optimum amount of product.

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. Typical regeneration temperatures are in the range of 250–700° C., desirably in the range of 350–700° C. Preferably, regeneration is carried out at a temperature range of 450–700° C.

It may be desirable to cool at least a portion of the regenerated catalyst to a lower temperature before it is directed to the conversion reactor or to the activation zone. A heat exchanger located externally to the regenerator may be used to remove some heat from the catalyst after it has been withdrawn from the regenerator. Another way is to contact the regenerated catalyst with a dilute acetone stream containing significant quantities of water to cool the catalyst. When the regenerated catalyst is cooled, it is desirable to cool it to a temperature which is from 20° C. higher to 200° C. lower than the temperature of the catalyst withdrawn from the regenerator. More desirably, it is cooled to a temperature from 100° C. to 200° C. lower than the temperature of the catalyst withdrawn from the regenerator. Introducing the cooled catalyst into the conversion reactor is one way to control the average temperature in the conversion reactor.

It is preferred that the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the conversion reactor or to the activation zone. Fresh catalyst can also be added to the conversion reactor independently of the regenerated or acetone contacted catalyst.

This invention will be better understood with reference to the following examples, which are intended to illustrate specific embodiments within the overall scope of the invention as claimed.

EXAMPLE 1

SAPO-34 molecular sieve, 50% by weight, aluminum chlorhydrol, 10% by weight, and UF grade kaolin clay, 40% by weight, was mixed with sufficient water to produce a slurry with approximately 40% by weight solids. The slurry was fed into a spray drier to form spray dried catalyst. The spray dried catalyst was analyzed by XRF (X-ray Fluorescence) spectroscopy. The amount of chlorine in the spray dried catalyst was 33,800 ppmw. The GAL Index of the un-calcined calcined catalyst was greater than 50.

EXAMPLES 2–4

Spray dried catalyst of Example 1 was heated in a nitrogen stream at temperatures of 600° C., 650° C. and 700° C. for one hour. The heat treated catalyst was then analyzed by XRF to determine the amount of residual chlorine remaining in the catalyst. Table 1 lists the residual chlorine content of each catalyst.

EXAMPLES 5–7

Spray dried catalyst of Example 1 was heated in a nitrogen stream at temperatures of 600° C., 650° C. and 700° C. for nine hours. The heat treated catalysts were then analyzed by XRF to determine the amount of residual chlorine remaining in each catalyst. Table 1 lists the residual chlorine content of each catalyst.

EXAMPLES 8

Spray dried catalyst of Example 1 was heated in a nitrogen stream at temperatures of 650° C. for five hours followed by heating in air at 650° C. for two hours. The heat treated catalyst was then analyzed by XRF to determine the amount of residual chlorine remaining in the catalyst. The chlorine content of the catalyst was 390 ppm by weight.

EXAMPLES 9–11

The spray dried catalyst of Example 1 was heated in a nitrogen stream at temperatures of 600° C., 650° C. and 700° C. for one hour followed by heating in air at 600° C., 650° C. and 700° C. for one hour, respectively. The heat treated catalysts were then analyzed by XRF to determine the amount of residual chlorine remaining in each catalyst. Table 1 lists the residual chlorine content of each catalyst.

TABLE 1

| Example No. | Temperature, ° C. | Sweep gas time, hrs | Sweep gas time, hrs | Chlorine, ppmw |
|---|---|---|---|---|
| 1 | n/a | n/a | n/a | 33,800 |
| 2 | 600 | N2/1 | N/A | 620 |
| 3 | 650 | N2/1 | N/A | 520 |
| 4 | 700 | N2/1 | N/A | 480 |
| 5 | 600 | N2/9 | N/A | 440 |
| 6 | 650 | N2/9 | N/A | 430 |

TABLE 1-continued

| Example No. | Temperature, °C. | Sweep gas time, hrs | Sweep gas time, hrs | Chlorine, ppmw |
|---|---|---|---|---|
| 7 | 700 | N2/9 | N/A | 350 |
| 8 | 650 | N2/5 | air/2 | 390 |
| 9 | 600 | N2/1 | air/1 | 510 |
| 10 | 650 | N2/1 | air/1 | 470 |
| 11 | 700 | N2/1 | air/1 | 430 |

EXAMPLE 12

The spray dried catalyst was heated at 600° C. in air for 120 minutes in an open container placed in an electrically heated muffle furnace. The calcined catalyst contained 1090 ppm chlorine (see Table 2).

EXAMPLE 13

The spray dried catalyst was heated at 650° C. in air for 120 minutes in an open container placed in an electrically heated muffle furnace. The calcined catalyst contained 730 ppm chlorine, and the GAL was 1.85 (see Table 2).

EXAMPLE 14

The spray dried catalyst was heated at 700° C. in air for 120 minutes in an open container placed in an electrically heated muffle furnace. The calcined catalyst contained 350 ppm chlorine (see Table 2).

EXAMPLE 15

The spray dried catalyst was heated at 600° C. in air for 120 minutes in an open container placed in an electrically heated muffle furnace. The calcined catalyst, 12 g, was placed in a ¾" OD stainless steel, packed bed tubular reactor that was electrically heated. About 1 g/min of steam was fed to the reactor maintained at a temperature of 600° C. The catalyst was heated in the presence of steam for 120 minutes. The chlorine content of the treated catalyst was 250 ppm (see Table 2).

EXAMPLE 16

The same procedure as in Example 15 was used except that the temperature was maintained at 650° C. for both the heating in air and heating in steam. The chlorine content of the treated catalyst was 140 ppm, and the GAL was 1.48 (see Table 2).

EXAMPLE 17

The same procedure as in Example 15 was used except that the temperature was maintained at 700° C. for both the heating in air and heating in steam. The chlorine content of the treated catalyst was 30 ppm (see Table 2).

EXAMPLE 18

The same procedure as in Examples 12 was used except that the catalyst was heated in air for 240 minutes. The chlorine content of the treated catalyst was 830 ppm (see Table 2).

EXAMPLE 19

The same procedure as in Examples 13 was used except that the catalyst was heated in air for 240 minutes. The chlorine content of the treated catalyst was 590 ppm (see Table 2).

EXAMPLE 20

The same procedure as in Examples 14 was used except that the catalyst was heated in air for 240 minutes. The chlorine content of the treated catalyst was 290 ppm (see Table 2).

EXAMPLE 21–26

The same procedure as in Examples 15 were used except the times and temperatures of heating in air and the times and temperatures of heating in steam as indicated in Table 2.

EXAMPLE 27

The spray dried catalyst was heated at 600° C. in air for 120 minutes in an open container placed in an electrically heated muffle furnace. The calcined catalyst then placed in a ¾" OD stainless steel, packed bed tubular reactor that was electrically heated. About 1 g/min of steam at about 1 atm was fed to the reactor maintained at a temperature of 600° C. The catalyst was heated in the presence of steam for 240 minutes. The chlorine content of the treated catalyst was 150 ppmw, and the GAL was 2.24 (see Table 2).

EXAMPLE 28

The same procedure as in Example 27 was used except the temperatures of heating in air and the steam treatment was 650° C. The chlorine content of the treated catalyst was 40 ppmw, and the GAL was 1.62 (see Table 2).

As summarized in Table 2, heating in air for 120 minutes at 600° C., 650° C. and 700° C. without a subsequent steam treatment reduces the chlorine content to 1090, 730 or 350 ppm respectively. Increasing the heating time to 240 minutes at 600° C., 650° C. and 700° C., results in the further reduction in chlorine content to 830, 590 or 290 ppm, respectively. As indicated only small amounts of additional chlorine is removed by a doubling of the heating time. For example, heating at 650° C. during the first 120 minutes reduces the chlorine content in the catalyst by about 98%, i.e., from 33,800 ppm to 730 ppm. Heating for a second 120 minutes reduces the remaining chlorine content by an additional 19%, i.e., from 730 ppm to 590 ppm.

Heating in air for 120 minutes followed by heating in the presence of steam for 120 minutes at temperatures of 600° C., 650° C., and 700° C. reduces the chlorine content to 250, 140 and 30 ppm, respectively. Increasing the time the catalyst is heated in air and steam to 240 minutes, respectively, has little affect on further reducing the chlorine content as shown by a comparison of Examples 15–17 with Examples 21–23, respectively.

Examples 24–26 indicate that increasing the time the catalyst is steam treated at a given temperature (650° C. in these examples) following the heat treatment in air for 120 minutes results in a yet greater reduction in chlorine content. The most dramatic reduction in chlorine content is made during the first 15 minutes of contacting the heat treated catalyst with steam. For example, comparison of Example 13 with Example 24 suggests that the chlorine content is reduced from 730 ppm to 230 ppm after an additional 15 minute steam treatment at 650° C. This amounts to an additional chlorine reduction of about 68%. Also, as indicated in Table 2 greater than 99% of the chlorine may be removed from the catalyst following the steam treatment of the catalyst.

TABLE 2

| Example No. | Temp. ° C. | Time (air) Min. | Time (steam) min. | GAL Index | Chlorine Ppmw |
|---|---|---|---|---|---|
| 1 | N/A | N/A | N/A | >50 | 33800 |
| 12 | 600 | 120 | 0 | | 1090 |
| 13 | 650 | 120 | 0 | 1.85 | 730 |
| 14 | 700 | 120 | 0 | | 350 |
| 15 | 600 | 120 | 120 | | 250 |
| 16 | 650 | 120 | 120 | 1.48 | 140 |
| 17 | 700 | 120 | 120 | | 30 |
| 18 | 600 | 240 | 0 | | 830 |
| 19 | 650 | 240 | 0 | | 590 |
| 20 | 700 | 240 | 0 | | 290 |
| 21 | 600 | 240 | 240 | | 220 |
| 22 | 650 | 240 | 240 | | 160 |
| 23 | 700 | 240 | 240 | | 40 |
| 24 | 650 | 120 | 15 | | 230 |
| 25 | 650 | 120 | 30 | | 120 |
| 26 | 650 | 120 | 60 | | 70 |
| 27 | 600 | 120 | 240 | 2.24 | 150 |
| 28 | 650 | 120 | 240 | 1.62 | 40 |

The attrition properties of Examples 1, 13, 16, 27, and 28 are listed in Table 2. Attrition properties of catalysts can be defined by the Gross Attrition Loss (GAL) Index. The smaller the GAL Index the more resistant to attrition is the catalyst. The GAL Index is measured in the following manner. About 6.0±0.1 g of SAPO catalyst was added to an attrition cup of an attrition apparatus known in the art. 23,700 scc/min of nitrogen gas was bubbled through a water-containing bubbler to humidify the $N_2$. The wet nitrogen passed through the attrition cup and exited the attrition apparatus through a porous fiber thimble. This thimble separates the fine catalyst particles resulting from the attrition of the catalyst particles in the attrition cup as the catalyst particles are circulated in the attrition cup by the fast flowing nitrogen gas. The pore size of the thimble determines the size of the fine particles that are separated from the catalyst. The pore size of the thimble used to measure the GAL Index was less than about 2 $\mu$m.

The nitrogen flow passing through the attrition cup was maintained for 60 minutes. The contents of the attrition cup were transferred to an elutriation cup. The elutriation cup is designed not to cause further attrition of the catalyst particles, but to remove any fine particles remaining in the attrition cup so that the fine particles may be included in the GAL Index. 23,700 scc/min of nitrogen gas was passed through the elutriation cup for 30 minutes. Additional fine particles were separated by the thimble. The collection of fine SAPO particles separated by the thimble were weighed. The amount in grams of fine particles divided by the original amount of catalyst added to the attrition cup is the GAL Index.

$$Gal\ index = C/(B+C) \times 100$$

wherein

B=weight of catalyst in elutriation cup
C=weight of collected fine catalyst particles

Having now fully described this invention, it will be appreciated by those skilled in the art that the invention can be performed within a wide range of parameters within what is claimed, without departing from the spirit and scope of the invention.

What is claimed is:

1. A method of removing halogen from a non-zeolitic molecular sieve catalyst comprising:
   heating the catalyst in a low moisture environment at a temperature from 400° C. to 1000°; and
   contacting the heated catalyst with steam at a temperature from 400° C. to 1000° C. to produce a steam-treated catalyst.

2. The method of claim 1 further comprising heating the steam-treated catalyst in an oxygen environment at a temperature from 400° C. to 1000° C.

3. The method of claim 1 wherein 50% by weight of the halogen is removed from the catalyst.

4. The method of claim 1 wherein the catalyst contains silicoaluminophosphate and/or aluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, and mixtures thereof.

5. The method of claim 1 wherein the low moisture environment contains less than 5% by volume water.

6. The method of claim 5 wherein the low moisture environment contains less than 1% by volume water.

7. The method of claim 1 wherein contacting the heated catalyst with steam comprises contacting the catalyst in an environment containing at least 10% by volume water.

8. The method of claim 1 wherein contacting the heated catalyst with steam removes from about 50% to 99% by weight of halogen from the heated catalyst.

9. The method of claim 8 wherein contacting the heated catalyst with steam removes from about 90% to about 99% by weight of halogen from the heated catalyst.

10. The method of claim 1 wherein the halogen is chlorine and the steam-treated catalyst contains from 10 ppm to 400 ppm by weight chlorine.

11. The method of claim 10 wherein the steam-treated catalyst contains from 10 ppm to 200 ppm by weight chlorine.

12. The method of claim 1 wherein the steam-treated catalyst has a GAL Index of less than 3.

13. A method of removing halogen from a non zeolitic molecular sieve catalyst comprising:
   heating the catalyst in an oxygen environment at a temperature from 400° C. to 1000° C. to produce a heated catalyst; and
   contacting the heated catalyst with steam at a temperature from 400° C. to 1000° C.

14. The method of claim 13 wherein the catalyst contains silicoaluminophosphate and/or aluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, and mixtures thereof.

15. The method of claim 13 wherein the oxygen environment contains greater than 10% by volume oxygen.

16. The method of claim 13 wherein contacting the heated catalyst with steam comprises contacting the catalyst in an environment containing at least 10% by volume water.

17. The method of claim 13 wherein the halogen is chlorine and contacting the heated catalyst with steam removes from 70% to 99% by weight of chlorine from the heated catalyst.

18. The method of claim 17 wherein contacting the heated catalyst with steam removes from 90% to 99% by weight of chlorine from the heated catalyst.

19. The method of claim 13 wherein the steam-treated catalyst contains from 10 ppm to 400 ppm by weight chlorine.

20. The method of claim 19 wherein the steam-treated catalyst contains from 10 ppm to 200 ppm by weight chlorine.

21. The method of claim 13 wherein the steam-treated catalyst has a GAL Index of less than 3.

22. A method of removing halogen from a halogen-containing non zeolitic molecular sieve catalyst, the method comprising heating the catalyst in an environment containing steam at a temperature from 400° C. to 1000° C., removing from 70% to 99.99% by weight of the halogen from the catalyst, thereby producing a steam-treated catalyst.

23. The method of claim 22 wherein the catalyst is heated at a temperature from 500° C. to 800° C.

24. The method of claim 22 wherein the catalyst is heated at a temperature from 550° C. to 700° C.

25. The method of claim 22 wherein the catalyst is heated for a period ranging from 0.1 to 5 hours.

26. The method of claim 25 wherein the catalyst is heated for a period ranging from 0.25 to 4 hours.

27. The method of claim 22 wherein the environment contains from 5% to 10% by volume water in the form of steam.

28. The method of claim 6 wherein the environment further contains air, nitrogen, helium, flue gas, or any combination thereof.

29. The method of claim 22 wherein the environment contains at least 10% by volume water in the form of steam.

30. The method of claim 29 wherein the environment further contains air, nitrogen, helium, flue gas, or any combination thereof.

31. The method of claim 22 wherein the halogen is chlorine.

32. The method of claim 22 wherein the source of halogen in the catalyst is aluminum chlorhydrol.

33. The method of claim 22 wherein the catalyst contains a silicoaluminophosphate and/or aluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, and mixtures thereof.

34. The method of claim 22 wherein the steam-treated catalyst contains from 10 ppmw to 200 ppmw by weight chlorine.

35. The method of claim 22 wherein the steam-treated catalyst has a GAL Index of less than 3.

36. The method of claim 22 further comprising contacting the steam-treated catalyst with an oxygen environment that contains greater than 5% by volume oxygen.

37. The method of claim 22 wherein, prior to heating the catalyst in an environment containing steam, the halogen-containing catalyst is heated in a low-moisture environment at a temperature of from 400° C. to 1000° C., removing at least 50% by weight of the halogen in the catalyst.

38. The method of claim 37 wherein the low moisture environment contains less than 5% by volume water.

39. The method of claim 38 wherein the low moisture environment contains less than 1% by volume water.

40. The method of claim 37 wherein the low moisture environment contains air, nitrogen, helium, flue gas, or any combination thereof.

41. A method of removing chlorine from a non-zeolitic molecular sieve catalyst comprising:
heating the catalyst in a low moisture environment at a temperature from 400° C. to 1000° C. to remove at least 50% by weight of the chlorine from the catalyst; and
contacting the heated catalyst in a second calcination environment containing about 5% to about 10% by volume water at a temperature from 400° C. to 1000° C.

42. The method of claim 1 wherein the catalyst contains silicoaluminophosphate and/or aluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, and mixtures thereof.

43. The method claim 41 wherein the low moisture environment contains less than 1% by volume water.

44. The method of claim 41 wherein contacting the heated catalyst in a second calcination environment produces a catalyst that contains from 10 ppmw to 400 ppm by weight chlorine.

45. The method of claim 41 wherein the steam-treated catalyst has a GAL Index of less than 3.

46. A catalyst comprising a non zeolitic molecular sieve, inorganic oxide matrix, and matrix material, wherein the catalyst contains from 10 ppm to 600 ppm by weight halogen.

47. The catalyst of claim 46 wherein the halogen is chlorine.

48. The catalyst of claim 47 wherein the catalyst contains from 10 ppmw to 200 ppmw chlorine.

49. The catalyst of claim 48 wherein the catalyst contains from 10 ppmw to 80 ppmw chlorine.

50. The catalyst of claim 46 wherein the catalyst has a GAL Index of less than 5.

51. The catalyst of claim 50 wherein the GAL Index is less than 3.

52. The catalyst of claim 46 wherein the non-zeolitic molecular sieve is selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, the metal containing forms of each thereof, and mixtures thereof.

53. The catalyst of claim 46 wherein the catalyst comprises 20% to 45% by weight non-zeolitic molecular sieve, 5% to 20% by weight of inorganic oxide matrix, and 20% to 70% by weight matrix material.

54. The catalyst of claim 53 wherein the catalyst comprises 25% to 42% by weight non-zeolitic molecular sieve, 8% to 15% by weight of inorganic oxide matrix, and 40% to 60% by weight matrix material.

55. The catalyst of claim 51 wherein the GAL Index is less than 2.

56. The catalyst of claim 46 wherein the inorganic oxide matrix comprises an aluminum oxide matrix.

57. The catalyst of claim 47 wherein the source of chlorine is aluminum chlohydrol.

* * * * *

UNITED STATES PATENT AND TRADEMARK OFFICE
CERTIFICATE OF CORRECTION

PATENT NO. : 6,440,894 B1
DATED : August 27, 2002
INVENTOR(S) : Luc Martens et al.

It is certified that error appears in the above-identified patent and that said Letters Patent is hereby corrected as shown below:

<u>Title page,</u>
Item [75], Inventors, should read as follows:
-- Inventors:   Luc R. Martens, Meise (BE); Stephen N. Vaughn, Kingwood, TX (US); Albert E. Shweizer, Baton Rouge, LA (US); John K. Pierce, Houston, TX (US); Shun C. Fung, Bridgewater, NJ (US) --

Signed and Sealed this

Seventeenth Day of February, 2004

JON W. DUDAS
*Acting Director of the United States Patent and Trademark Office*